United States Patent [19]
Willoughby et al.

[11] Patent Number: 5,847,002
[45] Date of Patent: Dec. 8, 1998

[54] COMPOSITIONS, FOR INHIBITION, CONTROL AND REGRESSION OF ANGIOGENESIS, CONTAINING HYALURONIC ACID AND NSAID

[75] Inventors: Derek A. Willoughby; Chandan Alam, both of London, England; Samuel Simon Asculai; Rudolf Edgar Falk, both of Toronto, Canada; David William Harper, Oakville, Canada

[73] Assignee: Hyal Pharmaceutical Corporation, Mississauga, Canada

[21] Appl. No.: 461,123

[22] Filed: Jun. 5, 1995

Related U.S. Application Data

[62] Division of Ser. No. 448,504, Jun. 5, 1995.

[30] Foreign Application Priority Data

Apr. 16, 1993 [CA] Canada ................... 2094203

[51] Int. Cl.$^6$ ............ A61K 31/195; A61K 31/19; A61K 31/045
[52] U.S. Cl. ............ 514/561; 514/570; 514/727
[58] Field of Search ............ 514/570, 561, 514/727

[56] References Cited

U.S. PATENT DOCUMENTS 5,095,037  3/1992  Iwamitsu et al. ............ 514/561

Primary Examiner—Theodore J. Criares
Attorney, Agent, or Firm—Ivor M. Hughes; Neil H. Hughes; Marcelo K. Sarkis

[57] ABSTRACT

The use of:

(a) a non-steroidal anti-inflammatory agent, and (b) hyaluronic acid and/or salts thereof and/or homologues, analogues, derivatives, complexes, esters, fragments, and subunits of hyaluronic acid, in the manufacture of a pharmaceutical composition for inhibiting, controlling and/or regressing angiogenesis in a therapy wherein dosage amounts taken from the composition each comprise:

(1) a therapeutically effective amount of component (a); and (2) a therapeutically effective amount of the hyaluronic acid and/or salts thereof and/or homologues, analogues, derivatives, complexes, esters, fragments, and sub-units of hyaluronic acid, the pharmaceutical composition being characterized in that for each dosage amount taken from the pharmaceutical composition, the amount of components (a) and (b) inhibit, control and/or regress angiogenesis.

6 Claims, 4 Drawing Sheets

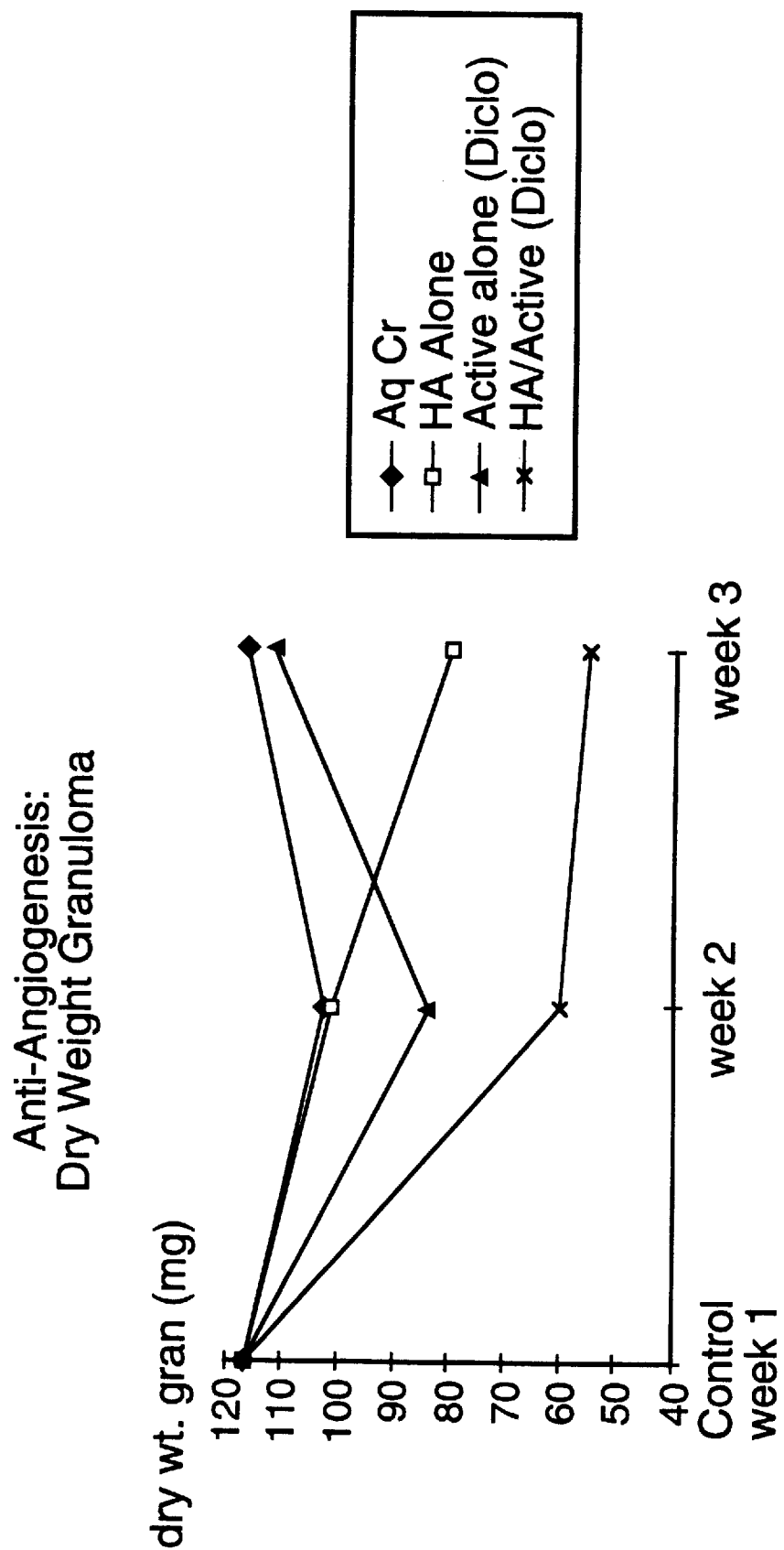

COMPOSITIONS, FOR INHIBITION, CONTROL AND REGRESSION OF ANGIOGENESIS, CONTAINING HYALURONIC ACID AND NSAID

This application is a divisional of application Ser. No. 08/448,504 filed Jun. 5, 1995 (status: Pending). Compositions, for inhibition, control and regression of angiogenesis, containing hyaluronic acid and NSAID.

FIELD OF INVENTION

This invention relates to the inhibition, control and regression of angiogenesis and finds one particular application in the inhibition of angiogenesis in cancer treatment for example as an adjuvant to known cancer treatments for prevention of metastasis.

BACKGROUND OF THE INVENTION

In an article entitled "Solid cores of tumors keeping out best drugs" by Sandra Blakeslee published in the Jul. 8, 1989 edition of the Globe and Mail, Toronto, Ontario, Ms. Blakeslee submitted that a growing number of researchers believe that a basic misunderstanding of the structure of solid tumors has led researchers into designing cancer drugs that are doomed to fail in many patients.

She relates that, Dr. Herberman, Director of the Pittsburgh Cancer Center, said that for decades, cancer researchers have simply developed drugs, put them in the bloodstream and assumed they would be carried to the tumor giving almost no consideration to how uniformly the drug is distributed once it reaches the tumor.

Her article also provided that according to Dr. Judah Folkman, a leading researcher on blood growth factors at the Harvard Medical School, for a long time, physicians have been taught that tumors outgrow their blood supply. According to the article that statement is not true. Tumors compress their blood supply. This compression makes it harder to administer drugs.

The article provides further that most people think a tumor is nothing but a collection of cancer cells. According to Dr. Jain, another researcher, in reality the tumor is only 50 per cent cells. The other half is blood vessels and interstitial space. Interstitial space in a tumor, he said, can be likened to the space between marbles packed in a box.

The article further provides that no matter how biological agents are mixed and administered, they must cross a blood-vessel wall and then cross the interstitium to reach their targets, cancer cells. The article continues that every tumor is different and there are different regions within each. Moreover, tumors change daily as they grow and rearrange parts. Most blood vessels inside tumors are highly disorganized as they take tortuous turns and grow peculiar attachments to nearby vessels.

In general, Dr. Jain said, as a tumor grows, its outer region recruits new blood vessels from surrounding normal tissue. (The tumour needs a blood supply to grow; metastasis also needs a blood supply to develop). The tumour also forms several abnormal blood vessels of its own. As the tumor grows in a confined space, many of the twisted blood vessels near its center are crushed. In turn, the tumor cells near them appear to die, although they grow into active cancer if transplanted into other animals. High pressures build up in these necrotic regions. Both blood vessels and liquid plasma in the interstitial spaces are squeezed. The pressure, therefore, prevents blood-borne molecules, including oxygen, from entering the central tumor areas.

Pressure is not uniform in normal tissue, Dr. Jain said, so a large molecule such as an antibody would reach its target through convection induced by pressure differences. But in the center of a tumor, pressure is uniformly high, blocking convection.

Molecules also migrate by diffusion Dr. Jain said, which is similar to the way a drop of ink spreads in water.

But he indicated that he measured antibody diffusion in tumours and found that it can take days, weeks or months for such large molecules to reach uniform concentration by diffusion in tumours. By then, it may be too late for treatments to do any good.

European Patent Application 0295092 purports to teach a vehicle together with fragments of hyaluronic acid for delivering of the fragments of hyaluronic acid into the skin to reach the dermal layer of the skin to increase the development of blood vessels for stimulating hair growth or regrowth. The preferred fragments of hyaluronic acid are polysaccharides containing from 7 to 25 monosaccharide units. The patent provides it is apparent that the larger the fragments of hyaluronic acid, the greater the difficulty there is in delivering the fragments to the dermal layer of the skin, unless there is also present in the composition a means for enhancing the activity of said fragments.

The combination may thus include a means for enhancing the activity of the fragments of hyaluronic acid especially to improve their penetration through the skin following topical application. Some activity enhancers, it is alleged, also function as vehicles for the fragments of the hyaluronic acid.

Some activity enhancers are also alleged to possess the ability to stimulate or increase hair growth. Minoxidil is asserted among others to be such an activity enhancer. Thus both the fragments of hyaluronic acid and minoxidil are alleged to stimulate hair growth both delivered by a vehicle.

There have been extensive studies to determine the defect in immune function that allows a tumor cell to develop. It was postulated initially by Jerne, and subsequently by Burnett that the immune system's major role was that of immunological surveillance to destroy abnormal cells. The concept of surveillance, while somewhat simplistic, remains an accepted concept for the elaborate mechanism of immune recognition and function that is present in the higher species—mammals.

It has then been postulated that tumors develop because of local or generalized immune suppression. However, as pointed out by Moller, if general immune suppression occurs, it is only certain types of neoplastic disorders that develop, mainly those of the lympho-reticular system. This observation is correct and represents a major challenge to the immune surveillance theory unless a specific reason can be shown as to why the individual cancer cell can develop plus individually evade the immune system.

It was demonstrated experimentally in 1974 that defects of macrophage function may exist in neoplastic disease.

The initial experiments found suppressor cells to be part of the immune system; these were either of the T-cell type of the macrophage cell system. There was presence demonstrated in neoplasia, chronic bacterial infection, recovery from massive injury and chronic fungal infection.

There has been repeated demonstration in experimental animals, that the macrophage cell function is altered in neoplastic disease. The macrophages in the animal's systems appeared "blocked" in their function. Generally when removed from the in vivo situation, washed in saline and cultured, they could perform normally. This block has been shown to be related to the excessive production of prostaglandin by neoplastic tissue or by the macrophage itself.

In the basic research efforts in the latter '70s and the early 80's, there existed considerable confusion as to what role immunotherapy should take in cancer. Activation or "hyping" of macrophages was thought to be important. However, in an examination by Romans and Falk of peritoneal macrophages obtained from patients with neoplastic disease, there was definite evidence that these macrophages were already activated yet were co-existing with cancer cells and not causing their destruction.

In the early part of this year it has been shown by several independent investigators that the malfunction of macrophages or the putitive block is due to excessive prostaglandin and that this can be altered in tissue culture by corticosteroids, ASA, and the non-steroidal anti-inflammatory drugs, i.e. indomethacin, and naproxen (Naprosy™). Again, in animal tumors it was repeatedly demonstrated that these substances could alter the response to neoplastic cells and that various combinations of these substances employed with immune enhancing agents could produce very credible success in eliminating experimental tumors. Lala and co-workers combined Indomethacin therapy with Interleukin 2 and showed that this could effect a cure with experiment neoplasm.

There were continued problems with the use of any of these agents in the actual human in vivo experience. All of the non-steroidal anti-inflammatory agents (NSAID) produced major toxicity in terms of gastro-intestinal, neurological, and other areas. Thus, the basis of the present approach is that under general circumstances the use of these agents in human disease, in sufficient amounts, the drug will penetrate to any pathological tissue to alter therapeutically local prostaglandin production. While intravenous preparations exist of Indomethacin and now of other agents, the data is overwhelming, as is our own experience, that using these drugs alone produces prohibitive side effects in human subjects. Therefore only insufficient amounts can be brought into the body systemically for example to effect more than occasional responses in neoplasm.

New blood vessel formation is essential for the development of tumours and chronic inflammatory granulomatous tissue such as pannus in rheumatoid arthritis. The restriction of angiogenesis in such disease states is a valid therapeutic target for the restriction of tissue growth.

Sub-retinal neovascularisation is a major ophthalmic problem in the western world today. A small percentage of patients are treated with laser photocoagulation when a sub-retinal new vessel grows from the middle choroidal layer of the eye under the retina, destroying macula or sharp vision. Most vessels grow too close to the center however, and a laser burn would therefore destroy any potential central vision.

Alpha interferon injections three times a week have also been proposed for the treatment of sub-retinal neovascularisation. The side effects however from the injections especially in elderly people are very significant, being detrimental to the procedure. Additionally, the logistics of arranging the injections from freshly made up preparations are very difficult, to say the least.

In arthritis, a pannus develops. In order for the pannus to develop, vascularization must be present as the pannus develops by the vascularization accompanied by deposition of corrective tissue beneath the corneal epithelium. One result is the overgrowth of connective tissue on the articular surface of the diarthrodial joint.

Applicants have now developed methods, and compositions suitable for use, for the inhibition of angiogenesis (the formation and differentiation of blood vessels) which finds among other applications two applications, the treatment of tumours and as an adjuvant to any cancer treatment for the inhibition of metastasis of the cancer. Applicants have also developed new methods and new compositions suitable for use for the regression of angiogenesis (the regression of blood vessel growth.

Applicant's invention can also be used for the treatment of other diseases and conditions whose successful treatment would benefit from inhibiting, controlling and/or regressing blood vessel growth for example, sub-retinal neovascularisation and the reduction of the effects of arthritis. If a person is prone to arthritis, the administration of pharmaceutical compositions according to Applicants' invention, for example systemically (for example by intravenous administration) may even prevent the arthritis or at least reduce the effects of the arthritis.

It is therefore an object of this invention to provide a method for the inhibition, control and regression of angiogenesis, compositions for the inhibition, control and regression of angiogenesis and the use of such compositions for the inhibition, control and regression of angiogenesis.

Further and other objects of the invention will realized by those skilled in the art from the following summary of the invention and detailed description of embodiments thereof.

SUMMARY OF THE INVENTION

According to one aspect of the invention, there is provided a process for the inhibition, control and/or regression of angiogenesis, (for example inhibition of blood vessel growth to a malignant tumour, cutting off blood vessel growth or development, in to a malignant tumour) in a mammal (for example a human), the process comprising the steps of administering an effective dosage amount of a pharmaceutical composition for the inhibition, control and/or regression of angiogenesis to a site on/in the mammal in need of inhibition, control and/or regression of angiogenesis usually over a number of weeks or months on a regular basis, each effective dosage amount of the composition comprising in (a homogeneous admixture) an effective non-toxic dosage amount of an NSAID (non-steroidal anti-inflammatory agent) for example diclofenac (for example dissolved in the composition) and an effective non-toxic dosage amount of hyaluronic acid and/or salt thereof (for example sodium hyaluronate) and/or homologues, analogues, derivatives, complexes, esters, fragments and/or sub-units of hyaluronic acid preferably sodium hyaluronate.

According to an embodiment of the invention the composition may be administered systemically (for example intravenously, intra arterially, intraperitoneally, intrapleurally, by direct injection into for example a tumour, and the like) and may be used as an adjuvant to any cancer treatment.

When an NSAID, for example indomethacin (dissolved in n-methyl glucamine), naproxen,(+/−) tromethamine salts of ketorolac, ibuproxen, piroxicam, propionic acid derivatives, acetylsalicylic acid, flunixin, diclofenac, diclofenac sodium or other NSAID is administered with greater than 200 mg of a form hyaluronic acid (for example 200–1,000 mg of sodium hyaluronate) for a 70 kg person with the effective amount of the NSAID (in one instance diclofenac), no major toxic side effects occur such as gastro-intestinal distress, neurological abnormalities, depression, etc., even at elevated amounts of the NSAID (if necessary). If the amount of hyaluronic acid is decreased below that amount, side effects may begin to occur.

According to another embodiment the composition may also be administered intradermally, applied topically for delivery into the skin, or administered rectally or put on a patch to be secured to the skin of the patient. Whatever the route of administration, the form is a homogeneous composition whether sterile water containing solution for systemic administration or a cream, lotion or gel for topical administration. Whatever the composition it may be packaged in an appropriate container (intravenous bag, vial for injection, tube or jar of cream).

According to another aspect of the invention the use of a combination of a form of hyaluronic acid (for example hyaluronic acid and/or salt thereof and/or a homologue, analogue, derivative, complex, ester, fragment and/or subunit of hyaluronic acid) (for example sodium hyaluronate) and a non-steroidal anti-inflammatory agent (NSAID), for example diclofenac sodium is provided for the inhibition, control and/or regression of angiogenesis.

In such use an effective non-toxic amount of a combination of the form of hyaluronic acid (for example sodium hyaluronate) and NSAID (for example diclofenac sodium) may be used for inhibition, control and regression of angiogenesis.

Thus an effective non-toxic dosage amount of a composition comprising an effective non-toxic dosage amount of sodium hyaluronate and a therapeutically effective non-toxic dosage amount of NSAID for example diclofenac sodium may be used to inhibit angiogenesis. The amount of NSAID (for example diclofenac) administered systemically may be about 15 to about 100 mg of NSAID for example 35 mg/70 kg person (1/2 mg/kg). The NSAID may be administered in larger amounts provided the amounts are non-toxic, for example to 420 mg/70 kg person (6 mg/kg). Where the NSAID is administered systemically (e.g. by injection, etc.) a guide with respect to the amount of the form of hyaluronic acid is that for every about 15 mg of NSAID, about 50 mg of the form of hyaluronic acid may be used (e.g. sodium hyaluronate).

For topical application the amount of the form of diclofenac sodium may be in excess of about 5–10 mg/cm$^2$ of skin or exposed tissue in the dosage amount to which the dosage amount of the composition is applied. The form of hyaluronic acid, for example sodium hyaluronate, may also be in excess of about 5–10 mg/cm$^2$ in each dosage amount.

Thus according to another aspect of the invention a pharmaceutical composition (suitable for systemic, and/or topical application [on the skin, rectally, on the mucosa, etc.]) is provided (for example a multigram pharmaceutical composition for use topically) effective for the inhibition, controlling and regression of angiogenesis, the pharmaceutical composition containing a plurality of dosage amounts for inhibiting, controlling and regression of angiogenesis, each said dosage amount comprising a therapeutically effective non-toxic (to the patient) dosage amount of the NSAID (for example diclofenac) and an effective non-toxic dosage amount of the hyaluronic acid and/or salts thereof and/or homologues, analogues, derivatives, complexes esters, fragments, and/or subunits of hyaluronic acid effective to inhibit, control and regress angiogenesis.

The pharmaceutical composition may comprise suitable excipients depending upon the route of administration for example sterile water (systemic administration), excipients to make a gel, lotion or cream (topical administration) or whatever may be the route (for example a solubilizer (such as methoxypolyethelene glycol 350) and a preservative such as benzyl alcohol).

According to yet another aspect of the invention, a dosage amount of a pharmaceutical composition is provided for inhibition, controlling and regressing of angiogenesis, the composition comprising:

(1) a non-steroidal anti-inflammatory agent (NSAID) for example diclofenac sodium; and (2) hyaluronic acid and/or salts thereof (for example sodium hyaluronate) and/or homologues, analogues, derivatives, complexes esters, fragments and subunits of hyaluronic acid characterized in that said composition:

(a) is in a dosage form (e.g. in a cream, lotion, gel, intravenous solution, injectable, etc.) which is suitable for administration (systemically or topically, etc.); and (b) is in such an amount and in such form that component (1) is in an effective dosage amount together with component(2) to inhibit, control and regress angiogenesis (for example which inhibits metastasis). The pharmaceutical composition may comprise a plurality of dosage amounts.

According to still another aspect of the invention the use of (1) a non-steroidal anti-inflammatory agent (NSAID) for example diclofenac sodium; and (2) hyaluronic acid and/or salts thereof and/or homologues, analogues, derivatives, complexes, esters, fragments and subunits of hyaluronic acid, in the manufacture of a pharmaceutical composition for use to inhibit, control and regress angiogenesis in mammals (for example in humans) is provided wherein dosage amounts may be taken from the composition and each dosage amount taken comprises:

a therapeutically effective non-toxic dosage amount of each of components (1) and (2) to inhibit, control and regress angiogenesis.

The composition containing the form of hyaluronic acid and NSAID provides greater inhibition, control and regression (significantly greater inhibition, control and regression) of angiogenesis than a composition comprising a form of hyaluronic acid (for example sodium hyaluronate) only (without an NSAID). Thus, according to another aspect of the invention Applicants have provided similar methods of treatment, pharmaceutical compositions, dosage amounts and uses comprising forms of hyaluronic acid (for example sodium hyaluronate having a molecular weight less than about 750,000 daltons) without the NSAIDS as it did with the forms of hyaluronic acid with the NSAIDS.

The amount of the form of hyaluronic acid (for example sodium hyaluronate) per dosage amount may vary from about 5 mg for human administration as for example topically (5 mg/cm$^2$ of skin or exposed tissue) depending on the route of administration to about 1,000 mg/70 kg person depending upon the route of administration. As there is not toxicity, the form of hyaluronic acid can obviously be administered in a dose excess (for example 3000 mg/70 kg person if administered systemically) without any adverse effects. Amounts of the form of hyaluronic acid (for example sodium hyaluronate) to be administered systemically may be about 50 for each 15 mg of NSAID. Preferably the form of hyaluronic acid (for example sodium hyaluronate) administered, has a molecular weight less than about 750,00 daltons (for example about 150,00 to about 225,000 daltons). While higher molecular weights of the hyaluronic acid and forms thereof may be used to inhibit angiogenesis, where the molecular weight of the hyaluronic acid chosen for use is very large, it is preferred that the form of hyaluronic acid is autoclaved, to break down the hyaluronic acid to fragments of lesser molecular weight or if feasible diluted to permit administration and ensure no coagulation (whatever the route of administration). Where the molecular weight of the form of the form of hyaluronic acid being employed is larger, the concentration of the form of the hyaluronic acid in the composition may be adjusted, for example be reduced (for example to less than about 1%) dependent on the molecular weight.

One form of hyaluronic acid and/or salts thereof (for example sodium salt) and homologues, analogues, derivatives, complexes, esters, fragments, and sub-units of hyaluronic acid, preferably hyaluronic acid and salts and thereof, suitable for use with Applicant's invention is a fraction supplied by Hyal Pharmaceutical Corporation. One such fraction is a 15 ml vial of Sodium hyaluronate 20 mg/ml (300 mg/vial—Lot 2F3). The sodium hyaluronate is a 2% solution with a mean average molecular weight of about 225,000. The vial also contains water q.s. which is triple distilled and sterile in accordance with the U.S.P. for injection formulations. The vials of hyaluronic acid and/or salts thereof may be carried in a Type 1 borosilicate glass vial closed by a butyl stopper which does not react with the contents of the vial.

The fraction of hyaluronic acid and/or salts thereof (for example sodium salt) and homologues, analogues, derivatives, complexes, esters, fragments, and sub-units of hyaluronic acid, preferably hyaluronic acid and salts thereof, may comprise hyaluronic acid and/or salts thereof having the following characteristics:

a purified, substantially pyrogen-free fraction of hyaluronic acid obtained from a natural source having at least one characteristic selected from the group (and preferably all characteristics) consisting of the following:

i) a molecular weight within the range of 150,000–225,000;

ii) less than about 1.25% sulphated mucopoly-saccharides on a total weight basis;

iii) less than about 0.6% protein on a total weight basis;

iv) less than about 150 ppm iron on a total weight basis;

v) less than about 15 ppm lead on a total weight basis;

vi) less than 0.0025% glucosamine;

vii) less than 0.025% glucuronic acid;

viii) less than 0.025% N-acetylglucosamine;

ix) less than 0.0025% amino acids;

x) a UV extinction coefficient at 257 nm of less than about 0.275;

xi) a UV extinction coefficient at 280 nm of less than about 0.25; and xii) a pH within the range of 7.3–7.9.

Preferably, the hyaluronic acid is mixed with water and the fraction of hyaluronic acid has a mean average molecular weight within the range of 150,000-225,000. More preferably, the fraction of hyaluronic acid comprises at least one characteristic selected from the group (and preferably all characteristics) consisting of the following characteristics:

i) less than about 1% sulphated mucopolysaccharides on a total weight basis;

ii) less than about 0.4% protein on a total weight basis;

iii) less than about 100 ppm iron on a total weight basis;

iv) less than about 10 ppm lead on a total weight basis;

v) less than 0.00166% glucosamine;

vi) less than 0.0166% glucuronic acid;

vii) less than 0.0166% N-acetylglucosamine;

viii) less than 0.00166% amino acids;

x) a UV extinction coefficient at 257 nm of less than about 0.23;

xi) a UV extinction coefficient at 280 nm of less than 0.19; and xii) a pH within the range of 7.5–7.7

Applicants also propose to use sodium hyaluronate produced and supplied by LifeCore™ Biomedical, Inc., having the following specifications:

| Characteristics | Specification |
| --- | --- |
| Appearance | White to cream colored particles |
| Odor | No perceptible odor |
| Viscosity Average Molecular Weight | <750,000 Daltons |
| UV/Vis Scan, 190–820 nm | Matches reference scan |
| OD, 260 nm | <0.25 OD units |
| Hyaluronidase Sensitivity | Positive response |
| JR Scan | Matches reference |
| pH, 10 mg/g solution | 6.2–7.8 |
| Water | 8% maximum |
| Protein | <0.3 mcg/mg NaHy |
| Acetate | <10.0 mcg/mg NaHy |
| Heavy Metals, maximum ppm | |

| As | Cd | Cr | Co | Cu | Fe | Pb | Hg | NI |
| --- | --- | --- | --- | --- | --- | --- | --- | --- |
| 2.0 | 5.0 | 5.0 | 10.0 | 10.0 | 25.0 | 10.0 | 10.0 | 5.0 |

| | |
| --- | --- |
| Microbial Bioburden | None observed |
| Endotoxin | <0.07 EU/mg NaHy |
| Biological Safety Testing | Passes Rabbit Ocular Toxicity Test |

Another form of sodium hyaluronate is sold under the name Hyaluronan HA-M5070 by Skymart Enterprises, Inc. having the following specifications:
Specifications' Test Results

| | |
| --- | --- |
| Lot No. | HG1004 |
| pH | 6.12 |
| Condroitin Sulfate | not detected |
| Protein | 0.05% |
| Heavy Metals | Not more than 20 ppm |
| Arsenic | Not more than 2 ppm |
| Loss on Drying | 2.07% |
| Residue on Ignition | 16.69% |
| Intrinsic Viscosity | 12.75 dl/s (XW: 679,000) |
| Nitrogen | 3.14% |
| Assay | 104.1% |
| Microbiological Counts | 80/g |
| E. coli | Negative |
| Mold and Yeast | Not more than 50/g |

Other forms of hyaluronic acid and/or its salts, and homologues, derivatives, complexes, esters, fragments and sub units of hyaluronic acid may be chosen from other suppliers, for example those described in prior art documents provided the form of hyaluronic acid chosen is suitable for transport of the medicine.

The following references teach hyaluronic acid, sources thereof, and processes for the manufacture and recovery thereof which may be suitable.

U.S. Pat. No. 4,141,973 teaches hyaluronic acid fractions (including sodium salts) having:

"(a) an average molecular weight greater than about 750,000, preferably greater than about 1,200,000—that is, a limiting viscosity number greater than about 1400 cm³/g., and preferably greater than about 2000 cm³/g.;

(b) a protein content of less than 0.5% by weight;

(c) ultraviolet light absorbance of a 1% solution of sodium hyaluronate of less than 3.0 at 257 nanometers wavelength and less than 2.0 at 280 nanometers wavelength;

(d) a kinematic viscosity of a 1% solution of sodium hyaluronate in physiological buffer greater than about 1000 centistokes, preferably greater than 10,000 centistokes;

(e) a molar optical rotation of a 0.1–0.2% sodium hyaluronate solution in physiological buffer of less than $-11 \times 10^3$ degree—$cm^2$/mole (of disaccharide) measured at 220 nanometers;

(f) no significant cellular infiltration of the vitreous and anterior chamber, no flare in the aqueous humour, no haze or flare in the vitreous, and no pathological changes to the cornea, lens, iris, retina, and choroid of the owl monkey eye when one milliliter of a 1% solution of sodium hyaluronate dissolved in physiological buffer is implanted in the vitreous replacing approximately one-half the existing liquid vitreous, said HUA being (g) sterile and pyrogen free and (h) non-antigenic."

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture.

BRIEF DESCRIPTION OF THE DRAWINGS

FIG. 4 illustrates graphically the results of tests relating to Anti-Angiogenesis: Dry Weight Granuloma.

DETAILED DESCRIPTION OF EMBODIMENTS

The invention will now be illustrated with reference to the following experimental data and tests performed.

The Applicants chose a simple model of murine angiogenesis induced with a chronic granulomatous reaction to Freund's complete adjuvant in croton oil. The Applicants assessed this process using a modification of this method by the formation of an intravascular cast incorporating carmine red. Chronic granulomatous air pouches were induced by the sc injection of 3 ml air into anaesthetized mice (25–30 g, Tuck Original) and 0.5 ml Freund's complete adjuvant with 0.1% croton oil 24 hours later. The mice were dosed for 6 days and the vascular content assessed by the formation of a vascular cast. This was formed by the intravenous injection of 1 ml 25% carmine red in 10% gelatin at 40° C. into warmed mice. This overcame any pharmacological or temperature-related alterations in peripheral vasomotor tone which may have invalidated the results. The carcasses were chilled and the granulomatous air pouch linings dissected. These were dried at 56° C., weighed, and papain digested. The dye was then be dissolved by the addition of 1 ml 0.05M NaOH, and the samples were then centrifuged at 2500 g for 20 minutes. After these were filtered, the absorbances were read at 490 nm using a multiwell plate reader (Biotek). The results were then expressed as either μg dye/mg dry weight of tissue.

The Applicants have tested whether the topical application of diclofenac/hyaluronan (HA)—e.g. sodium hyaluronate whose molecular weight was less than 750,000 daltons, would have angiostatic activity and whether the HA e.g. sodium hyaluronate alone would have angiostatic static activity.

Figure 1A:
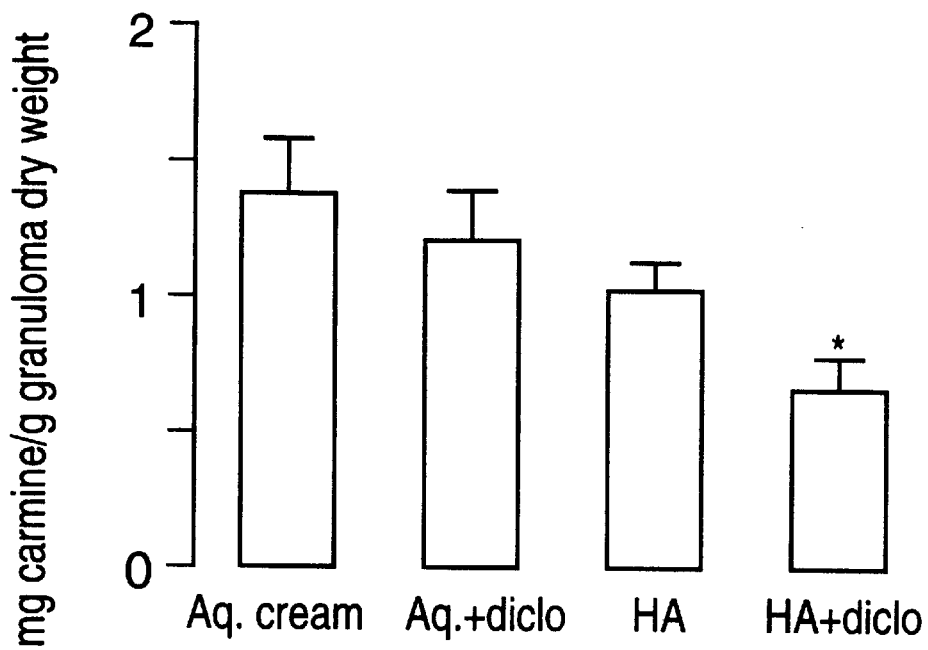
FIG. 1 comprises two FIGS. 1(a) and 1(b) which are bar graphs illustrating the effect of formulations on the vasculature within the murine chronic granulomatous air pouch.
Figure 1B:
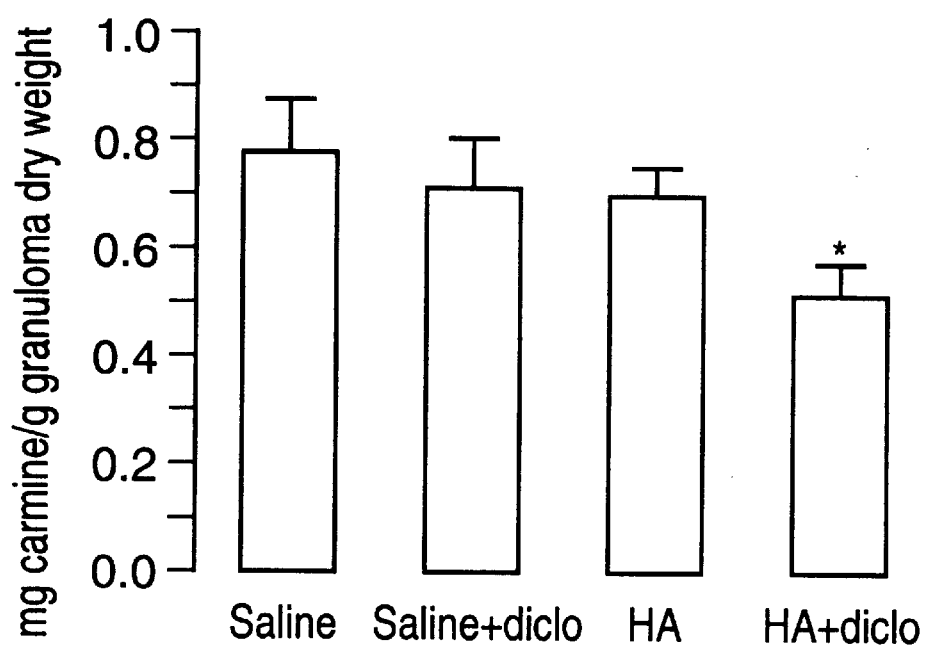

Topical applications of 0.1 ml hyaluronan and diclofenac (6 mg/kg) were made daily to the surface of the depilated air pouch. Diclofenac, when administered alone, was given with carboxymethylcellulose. The intra-lesional application was carried out by injection into the air pouch, diclofenac alone being administered in sterile saline. On the seventh day after induction the vascularity of the tissue was assessed. FIGS. 1(a) and 1(b) show that both the topical and intra-lesional administration of hyaluronan (HA) alone and diclofenac (diclo) alone exhibited no significant effect on the tissue vascularity. However, the combination of hyaluronan (HA) and diclofenac (diclo) produced a significant reduction in vascularity. (FIGS. 1(a) and 1(b) illustrate the effect of hyaluronan and diclofenac, alone or in combination on the development of the vasculature within the murine chronic granulomatous air pouch. Topical applications of 0.1 ml hyaluronan and diclofenac (6 mg/kg) were made daily to the surface of the depilated air pouch ether alone or in combination (FIG. 1(a)). Diclofenac alone was given in carboxymethylcellulose as vehicle. Intra-lesional application was carried out by injection into the air pouch (FIG. 1(b)). In this instance diclofenac was given in saline. On the seventh day the vascularity of the tissue was assessed).

PROTOCOL FOR TOPICAL AND INTRA-POUCH ADMINISTRATION OF HYALURONIC ACID AND DICLOFENAC IN COMBINATION

Introduction:

The formation of a subcutaneous air pouch in the dorsum of mice allows the formation of a lining which responds to produce a chronic inflammatory lesion in response to various antigens, irritants and foreign bodies. It can also be used for the introduction of drugs and various other treatments into the site of inflammation and the collection of inflammatory exudate.

A unique and simple technique has been perfected which quantitatively assesses angiogenesis in the developing inflammatory air pouch, by making a vascular cast incorporating carmine which can then be spectrophotometrically assayed.

Method:

For this experiment female mice (TO, 25–30 g, 10 per group) were lightly anesthetized with hypnorm/hypnoval. Air pouches were formed by the subcutaneous injection of 3 ml of filter-sterilized air, into the dorsum of each mouse. After 24 hours, chronic inflammation was induced in the air pouch lining by the injection of 0.5 ml Freund's complete adjuvant (FCA) supplemented with 0.1% croton oil.

Dosing Schedule:

Animals were dosed daily from the time of injection of FCA/croton oil, for 6 Days. At which point the analysis was performed.

1. Topical: (See Table One: Topical Application)

Four groups, 0.1. ml Aqueous Cream * (Thornton & Ross Ltd.)

0.1 ml Aqueous Cream+6 mg/kg Diclofenac (HPC lot.9113003)

0.1 ml Hyaluronic Acid (sodium hyaluronate)

(Hyal Pharmaceutical Corporation (HPC)) lot.OG019

0.1 ml Hyaluronic Acid (1% solution sodium hyaluronate, M.W. less than 750,000 daltons—e.g. 225,000 daltons) +6 mg/kg Diclofenac Before the topical application the hair on the dorsum was removed using hair clippers and depilatory cream (Louis Marcel). The skin surface was broken in one or two mice in each group, while using the electric clippers. These animals were discarded from the results.

2. Intra-Pouch:(Injection)

Four groups, 0.1 ml Sterile Saline (0.9%)

0.1 ml Sterile Saline+6 mg/kg Diclofenac (HPC lot.9113003)

0.1 ml Hyaluronic Acid (sodium hyaluronate) (HPC lot.OG019)

0.1 ml Hyaluronic Acid (1% solution, M.W. less than 750,000 daltons–e.g. 225,000 daltons)+6 mg/kg Diclofenac Vascular Casting:

Mice were anesthetized with hypnorm/hypnoval and placed on a heated operating platform maintained at 37° C. for 20 minutes. Each mouse was then placed into a water jacketed incubation chamber at 37° C. and injected i.v. with 1 ml of 15% carmine dye in 10% gelatin (in Hanks balanced salt solution) with syringe and solution prewarmed to 40° C. Cadavers were then chilled at 4° C. for 4 hours.

Analysis

The granulomatous tissue was dissected free and dried in an oven at 56° C. for 48 hours. The dried granuloma was weighed and then digested in 9 ml of papain solution (12-Units/ml in 0.05M phosphate buffer, pH 7.0, supplemented with 0.33g/l N-acetyl cysteine), at 56° C. for 48 hours. The digests were then made up to 10 ml with 5.0M NaOH and vortexed, to solubilise the dye and centrifuged. The digests were filtered through 0.2 $\mu$m cellulose nitrate membranes and 200 ml samples aliquoted into 96 well plates and analyzed for dye content by spectrophotometric analysis at 490 mm using a microplate reader. Vascular volume was calculated as carmine content per mg dry mass of tissue.

*Commercially available water based cream.

TABLE ONE

| | | | | Topical Application | | | | |
|---|---|---|---|---|---|---|---|---|
| Animal | Dry wt (mg) | Absorbness | mg carmine | ug/dye/mg | Dry wt (mg) | Absorbness | mg carmine | ug/dye/mg |
| | | Aqueous cream (0.1 ml) | | | | Hyaluronic acid (0.1 ml) (1% solution (10 mg/ml), M.W. less than 750,000 daltons) | | |
| 1 | 174 | .0383 | 65.5 | .376 | 187 | 0657 | 246 | 1.336 |
| 2 | 303 | 0.848 | 319 | 1.053 | 178 | 0.528 | 397 | 3.307 |
| 3 | 133 | 0.613 | 229 | 1.722 | 146 | 0.148 | 52.2 | 0.358 |
| 4 | 163 | 0.769 | 289 | 3.773 | 390 | 0.433 | 363 | 0.847 |
| 5 | | | | | | | | |
| 6 | 223 | 1.034 | 382 | 1.728 | 181 | 0.505 | 188 | 1.039 |
| 7 | 330 | 0.689 | 258 | 3.985 | 379 | 0.494 | 184 | 3.028 |
| 8 | 122 | 0.606 | 227 | 1.661 | 160 | 0.567 | 232 | 1.325 |
| 9 | | | | | 192 | 0.631 | 263 | 1.229 |
| 10 | 191 | 0.413 | 156 | 0.817 | | | | |
| MEAN | 179.6 | | 240.7 | 3.389 | 176.62 | | 184.5 | 1.031 |
| S.e.m. | 21.26 | | 346 | 0.201 | 561 | | 31.3 | 0.111 |
| p = | | | | | NS | | NS | NS |
| | | Hyaluronic acid (1% solution) + diclo(6 mg/kg) | | | | Aqueous cream + diclo(6 mg/kg) | | |
| 1 | 152 | 0.185 | 66.2 | 0.436 | 126 | 0.528 | 218 | 1.730 |
| 2 | 176 | 0.125 | 43.4 | 0.242 | 176 | 0.420 | 156 | 0.886 |
| 3 | 201 | 0.441 | 164 | 0.816 | 140 | 0.401 | 148 | 1.057 |
| 4 | 149 | 0.461 | 171 | 1.148 | | | | |
| 5 | 196 | 0.578 | 216 | 1.102 | 124 | 0.510 | 190 | 1.532 |
| 6 | | | | | 167 | 0.464 | 173 | 1.035 |
| 7 | 88 | 0.176 | 62.8 | 0.714 | | | | |
| 8 | 131 | 0.195 | 70.1 | 0.535 | 197 | 0.808 | 304 | 1.534 |
| 9 | 135 | 0.109 | 37.3 | 0.276 | 207 | 0.854 | 231 | 1.551 |
| 10 | | | | | 193 | 0.217 | 78.2 | 0.405 |
| Mean | 154.6 | | 103.6 | 0.658 | 166.3 | 187.3 | | 1.216 |
| S.e.m | 13.79 | | 24.3 | 0.123 | 11.58 | | 23.6 | 0.158 |
| p = | NS | | 0.0104* | 0.0209* | NS | | NS | NS | n = X
(diclo = Diclofenac)

TABLE TWO:

| | | | | Intra - pouch | | | | |
|---|---|---|---|---|---|---|---|---|
| Animal | Dry wt (mg) | Absorbness | mg carmine | ug/dye/mg | Dry wt (mg) | Absorbness | mg carmine | ug/dye/mg |
| | | Hyaluronic Acid (1% solution) + diclo(6 mg/kg) | | | | Hyaluronic Acid (1% solution) | | |
| 1 | 104 | 0.323 | 68 | 0.654 | 126 | 0.607 | 130 | 1.032 |
| 2 | 106 | 0.293 | 61.5 | 0.580 | 128 | 0.209 | 43.3 | 0.337 |
| 3 | 140 | 0.215 | 44.6 | 0.319 | 142 | 0.710 | 152 | 1.069 |

TABLE TWO:-continued

| | | | Intra - pouch | | | | | |
|---|---|---|---|---|---|---|---|---|
| Animal | Dry wt (mg) | Absorbness | mg carmine | ug/dye/mg | Dry wt (mg) | Absorbness | mg carmine | ug/dye/mg |
| 4 | 133 | 0.305 | 64.1 | 0.482 | 108 | 0.603 | 129 | 1.194 |
| 5 | 115 | 0.460 | 97.7 | 0.846 | 118 | 0.414 | 87.8 | 0.747 |
| 6 | 90 | 0.258 | 53.9 | 0.602 | 97 | 0.293 | 61.8 | 0.637 |
| 7 | 262 | 0.271 | 56.8 | 0.217 | 134 | 0.190 | 39.2 | 0.294 |
| 8 | 72 | 0.178 | 36.6 | 0.509 | 160 | 0.494 | 105 | 0.654 |
| 9 | 64 | 0.171 | 35.1 | 0.545 | 147 | 0.495 | 105 | 0.716 |
| 10 | 95 | 0.210 | 43.5 | 0.512 | 130 | 0.318 | 66.9 | 0.517 |
| MEAN | 117.1 | | 56.2 | 0.5266 | 329 | | 91.97 | 0.7197 |
| S.e.m. | 17.8 | | 5.85 | 0.0546 | 5.85 | | 12.24 | 0.0957 |
| p = | 0.0454* | | 0.0029** | 0.0260* | NS | | NS | NS |
| | | Saline | | | | Saline + diclo(6 mg/kg) | | |
| 1 | 211 | 0.919 | 197 | 0.932 | 139 | 0.773 | 166 | 1.194 |
| 2 | 98 | 0.590 | 126 | 1.282 | 158 | 0.242 | 50.5 | 0.320 |
| 3 | 135 | 0.390 | 82.6 | 0.614 | 99 | 0.730 | 156 | 1.577 |
| 4 | 161 | 0.880 | 101 | 1.184 | 99 | 0.400 | 104 | 1.050 |
| 5 | 117 | 0.482 | 103 | 0.880 | 129 | 0.409 | 86.7 | 0.674 |
| 6 | 134 | 0.587 | 125 | 0.932 | 124 | 0.262 | 54.8 | 0.442 |
| 7 | 138 | 0.447 | 94.9 | 0.686 | 162 | 0.402 | 85.2 | 0.526 |
| 8 | 233 | 0.398 | 84.3 | 0.361 | 135 | 0.303 | 63.7 | 0.471 |
| 9 | 109 | 0.438 | 93 | 0.854 | 170 | 0.468 | 99.5 | 0.586 |
| 10 | 168 | 0.220 | 45.7 | 0.272 | 122 | 0.292 | 61.3 | 0.520 |
| Mean | 150.4 | | 114.3 | 0.7988 | 133.7 | | 92.75 | 0.7363 |
| S.e.m | 13.8 | | 15.1 | 0.1022 | 7.75 | | 12.77 | 0.1275 |
| p = | | | | | NS | | NS | NS |

N = 10

TABLE THREE

| | Results | | | | | | | | |
|---|---|---|---|---|---|---|---|---|---|
| | Carmine dye (ug) | | | Granuloma dry wt. (mg) | | | ug. dye/g. gramuloma | | |
| Topical | Mean | S.e.m. | p = | Mean | S.e.m. | p = | Mean | S.e.m. | p = |
| Aq. cream | 240.7 | 34.6 | | 179.6 | 21.3 | | 1.389 | 0.201 | |
| aq + diclo | 187.3 | 23.6 | NS | 166.3 | 11.6 | NS | 1.216 | 0.158 | NS |
| HA | 184.3 | 21.3 | NS | 176.6 | 5.6 | NS | 1.031 | 0.111 | NS |
| HA + diclo i-pouch | 103.6 | 24.3 | 0.0104* | 154.6 | 13.8 | NS | 0.658 | 0.123 | 0.0209* |
| Saline | 114.3 | 15.1 | 150.4 | 13.8 | | 0.7988 | 0.1022 | | |
| Control + diclo | 92.6 | 12.8 | NS | 133.7 | 7.8 | NS | 0.7363 | 0.1229 | NS |
| MA | 91.9 | 12.5 | NS | 129 | 5.9 | NS | 0.07197 | 0.0957 | NS |
| HA + diclo | 56.2 | 5.85 | 0.0029** | 117.1 | 17.8 | 0.0454* | 0.5266 | 0.0546 | 0.0260* | n = 8 for Topical application
n = 10 for Intra -pouch treatment

This data supports the conclusion of HA and Diclofenac, in combination, acting synergistically as an angiostatic agent. Also, it is important to note that although not significant, the trend is such that HA+diclo is more angiostatic than HA alone, the latter being more potent than diclo.

All the data has been included for statistical analysis, if however one excludes "obvious" flyers, e.g. table two, animal 7, HA+diclo, the results are more significant.

The results of the tests and experiments firmly establish that forms of hyaluronic acid (for example sodium hyaluronate having a molecular weight less than 750,000 daltons—e.g. 225,000 daltons) and NSAID (for example diclofenac) act to inhibit angiogenesis, in example the granuloma resulting in a reduction in granuloma dry weight.

The inhibition of angiogenesis may be used in the treatment and destruction of cancerous tumours. The compositions, dosage amounts taken from the compositions, processes and treatments by the invention may be used as an adjuvant to any anti-cancer treatment (for example radiation, chemotherapy using anti-cancer drugs, etc.) The invention may also be used to prevent metastasis in cancer patients so that while one tumour is being eradicated, no other malignant tumours develop. Thus the development of tumours is inhibited by inhibition of blood vessel growth to a tumour (cutting off the supply of blood vessels to the tumour). In this regard use of the invention counters, opposes, interferes with and inhibits resulting activity by Tumour Angiogenesis Factor (TAF) produced by a cancerous tumour to increase blood vessel growth to such tumour, thereby inhibiting such growth. A composition, for example comprising sodium hyaluronate and diclofenac administered systemically to a human patient inhibits angiogenesis and the tumour is eradicated. The composition may be administered over a short term or a longer term as required (for example a number of weeks or months as required).

It appears from these initial investigations that the combination of hyaluronan and diclofenac, given either topically or directly into the lesion, results in reduced vascular development during granulomatous inflammation.

FURTHER PROTOCOL

In another protocol, the use of the air pouch on the mice was once again employed. Only this time, after formation of the pouches and injection of 0.5 ml Freund's complete adjuvant (FCA) supplemented with 0.1% croton oil, the granuloma in the mice were permitted to grow for 7 days (they were left unhealed for 1 week). The result was the growth of new blood vessels.

Some of the mice were sacrificed at the end of the 7 day period (in the same manner as previously described) while others were treated topically (dosed daily) with:

0.1 ml aqueous cream (Thornton & Ross Ltd.)

0.1 ml aqueous cream+6 mg/kg diclofenac (HPC Lot 9113003)

0.1 ml hyaluronic acid (HPC Lot 0G019)

0.1 ml hyaluronic acid (1% solution sodium hyaluronate, molecular weight less than 750,000 daltons—e.g. 225, 000 daltons)+6 mg/kg diclofenac Some of the mice were sacrificed (in the same manner) after 2 weeks (one week after the commencement of the topical application) and the remainder sacrificed (in the same manner) after 3 weeks (two weeks after the commencement of the topical application).

The carmine red dye displaced the blood in the granulomatous tissue. The granulomatous tissue was dissected and treated as previously described. The weight of the granuloma (including the carmine red dye) and weight of the carmine red dye (which displaced the blood) were determined for each mouse sacrificed at each stage (after 7, 14 and 21 days). The vascularity index (VI) was calculated and the mean vascularity index was calculated for each group as follows:

$$\text{Vascularity Index (VI)} = \frac{\text{weight of carmine red dye in GRANULOMA}}{\text{Weight of GRANULOMA (including carmine red dye)}}$$

From the following table it can be seen that with both the hyaluronic acid (HA) and HA/diclo combination, the mean dry weight of the granuloma decreased over time. With the HA/diclo composition, the vascularity index (VI) decreased (reduced) over time.. This did not occur with any other composition tested. It is therefore clear, this decrease (reduction) is a measure of the REDUCTION in vascularity (blood supply).

TABLE FOUR

The results for all mice sacrificed at one time were dealt with together

|  |  | Carmine (ug) | Dry wt. gran. (mg) | VI (ug/mg) |
|---|---|---|---|---|
| 1 week air pouch | mean | 173.55 | 116.71 | 1.5D5 |
|  | s.e.m. | 6.86 | 4.56 | 0.062 |
|  | p = | — | — | — |
| 2 week aqueous cream | mean | 127.87 | 102.65 | 1.228 |
|  | s.e.m. | 17.98 | 7.33 | 0.066 |
|  | p = | 0.0451* | NS | NS |
| 3 week aqueous cream | mean | 212.72 | 116.57 | 1.822 |
|  | s.e.m. | 10.66 | 3.49 | 0.062 |
|  | p = | 0.0141* | NS | 0.0046** |
| 2 week HA | mean | 115.70 | 101.23 | 1.136 |
|  | s.e.m. | 17.12 | 6.56 | 0.141 |
|  | p = | 0.0153 | 0.0328* | 0.0436* |

TABLE FOUR-continued

The results for all mice sacrificed at one time were dealt with together

|  |  | Carmine (ug) | Dry wt. gran. (mg) | VI (ug/mg) |
|---|---|---|---|---|
| 3 week HA | mean | 118.68 | 80.1 | 1.402 |
|  | s.e.m. | 14.97 | 5.44 | 0.138 |
|  | p = | 0.0075** | 0.0001*** | NS |
| 2 week aq. cream/ Diclo | mean | 108.63 | 84.41 | 1.300 |
|  | s.e.m. | 8.98 | 5.58 | 0.089 |
|  | p = | 0.0084*** | 0.0006*** | NS |
| 3 week aq. cream/ Diclo | mean | 150.07 | 112.19 | 1.353 |
|  | s.e.m. | 12.07 | 7.79 | 0.115 |
|  | p = | NS | NS | NS |
| 2 week HA/Diclo | mean | 69.63 | 60.23 | 1.196 |
|  | s.e.m. | 8.61 | 7.72 | 0.141 |
|  | p = | 0.0002*** | 0.0003*** | 0.0376* |
| 3 week HA/Diclo | mean | 66.63 | 55.31 | 1.125 |
|  | s.e.m. | 15.00 | 8.47 | 0.212 |
|  | p = | 0.0002* | 0.0002* | 0.0224* | s.e.m. = standard error mean
p = confidence

Figure 2:
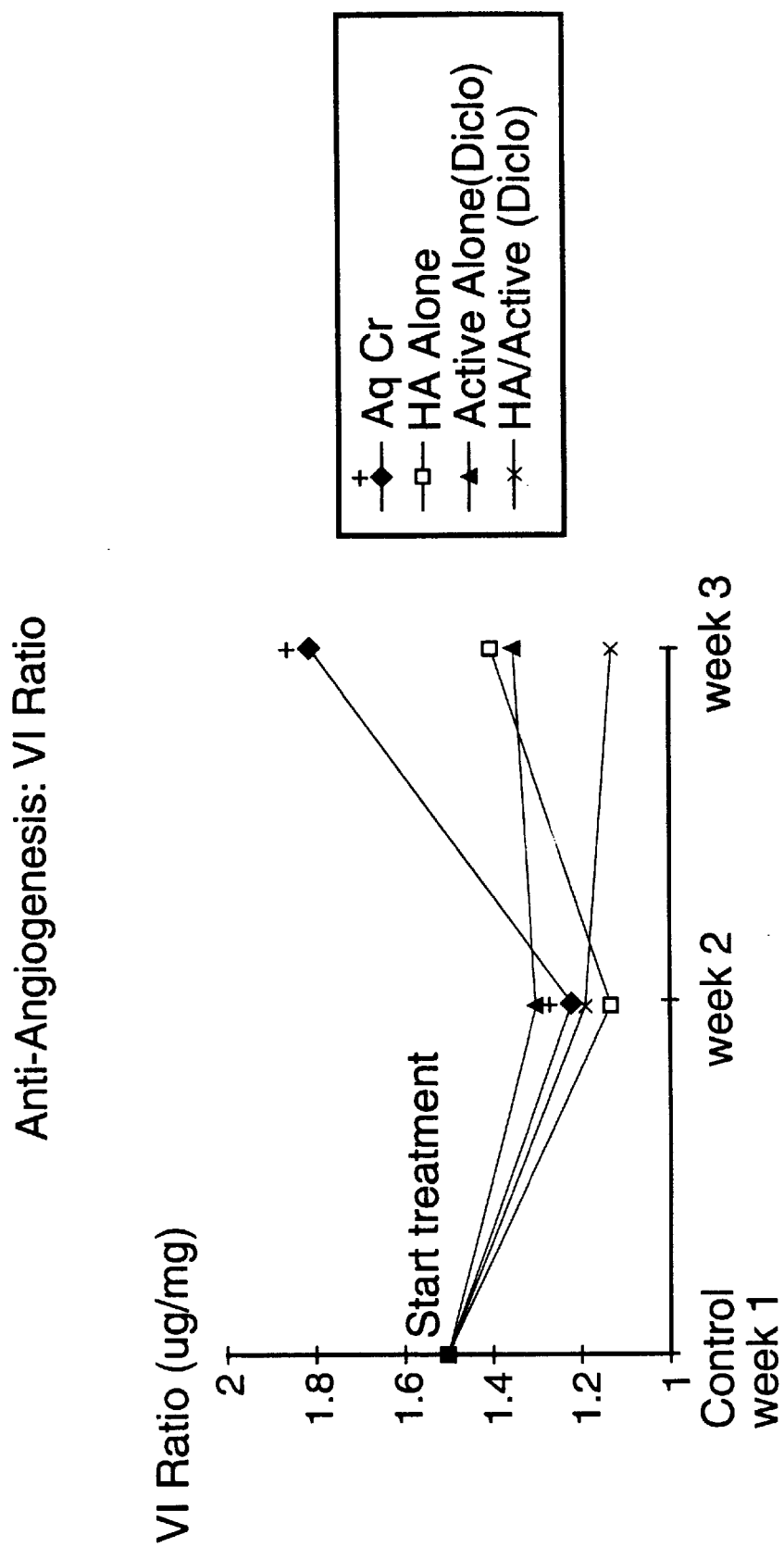
FIG. 2 illustrates graphically the results of tests relating to Anti-Angiogenesis: VI Ratio.
Figure 3:
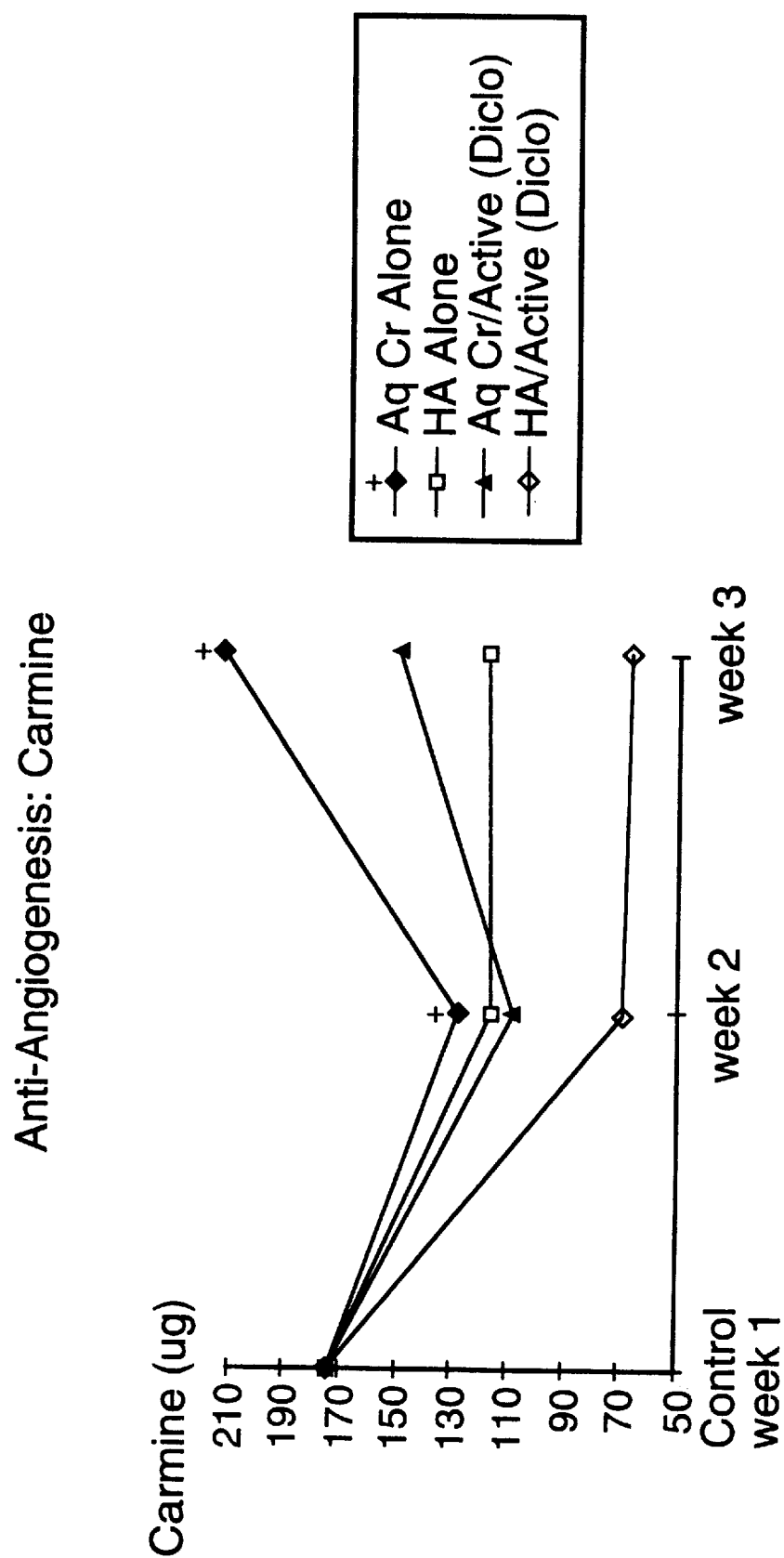
FIG. 3 illustrates graphically the results of tests relating to Anti-Angiogenesis: Carmine.

For better illustration, the results are shown in the graphs in FIGS. 2, 3 and 4 which teach FIG. 2 "Anti-angiogenesis": VI Ratio FIG. 3 "Anti-angiogenesis": Carmine FIG. 4 "Anti-angiogenesis": Granuloma Table Five is also provided setting out the means data in close proximity to one another for ease of comparison and upon which the graphs in FIGS. 2, 3 and 4 were prepared.

TABLE FIVE

|  | Control week 1 | week 2 | week 3 |
|---|---|---|---|
|  | Carmine (ug) |  |  |
| Aq. Cr. alone | 173.55 | 127.87 | 212.72 |
| HA alone | 173.55 | 115.7 | 118.68 |
| Aq. Cr./Diclo | 173.55 | 108.63 | 150.07 |
| HA/Diclo | 173.55 | 69.63 | 66.63 |
|  | dry weight granuloma (mg |  |  |
| Ag. Cr. | 116.71 | 102.65 | 116.57 |
| HA alone | 116.71 | 101.23 | 80.1 |
| Diclo Alone | 116.71 | 84.41 | 112.19 |
| HA/Diclo | 116.71 | 60.23 | 55.31 |
|  | VI (ug/mg) |  |  |
| Aq. cr. | 1.505 | 1.228 | 1.822 |
| HA alone | 1.505 | 1.136 | 1.402 |
| Diclo Alone | 1.505 | 1.3 | 1.353 |
| HA/Diclo | 1.505 | 1.196 | 1.125 |

The data with respect to the sodium hyaluronate composition administered to the mice was extrapolated for application to humans. The calculations below are not meant to mean that substantial regression would not be achieved by lesser amounts. In this regard the 0.1 ml solution of 1% HA solution administered with 6 mg/kg of Diclofenac to the 25–30 gm mice translates to 33.3 mg HA/kg and 6 mg Diclofenac sodium/kg. Thus a 70 kg person would have been administered in excess of 2200 mg of HA and 420 mg of Diclofenac.

It will also be appreciated by those skilled in the art that the processes, uses, compositions and dosage forms according to aspects of the invention may be applied to inhibit angiogenesis in other instances where inhibition of angiogenesis is desired, for example sub-retinal neovascularisation and for the treatment of arthritis or the prevention of further damage thereby including the prevention of the further development of pannus. It is therefore clear that many uses can be made of embodiments and aspects of this invention without departing from the scope thereof. It is therefore intended that all material contained herein be interpreted as illustrative of the invention and not in a limiting sense.

The embodiments of the invention in which an exclusive property or privilege is claimed are as follows:

1. A container containing a composition for administration to a human for the inhibition, control and regression of angiogenesis in humans, the composition comprising a synergistic effective amounts of (a) at least one dosage amount, each such dosage amount comprising a form of diclofenac selected from the group consisting of diclofenac and diclofenac sodium and (b) a form of hyaluronic acid selected from the group consisting of hyaluronic acid and sodium hyaluronate, each dosage amount comprising an effective non-toxic dosage amount of each of the form of diclofenac and a form of hyaluronic acid to inhibit, control and regress angiogenesis in a human and wherein the effective amount of the form of hyaluronic acid is about 50 mg for each of about 15 mg of the form of diclofenac in each dosage amount to be administered and, wherein the form of hyaluronic acid has a molecular weight less than about 750,000 daltons and greater than 150,000 daltons.

2. The container of claim 1 wherein the composition is for systemic administration.

3. A dosage amount of a pharmaceutical composition to inhibit, control or regress angiogenesis in humans, in the treatment of a disease or condition which would benefit from inhibiting, controlling or regressing angiogenesis, the dosage amount of the pharmaceutical composition comprising a synergistic effective amounts of:

(1) a form of diclofenac selected from the group consisting of diclofenac and diclofenac sodium, and (2) a form of hyaluronic acid selected from hyaluronic acid and its non-toxic salts, said form of hyaluronic acid having a molecular weight less than 750,000 daltons and greater than 150,000 daltons in a form suitable for administration to humans; characterized in that said composition comprises an effective angiogenesis inhibiting, controlling or regressing dosage amount of components (1) and (2) wherein component (2) exceeds about 50 mg for each 15 mg of component (1).

4. The dosage amount of claim 3 wherein component (2) is in an amount of about 2200–2800 mg.

5. The dosage amount of claim 3 wherein the form of hyaluronic acid is sodium hyaluronate.

6. The dosage amount of claim 3, 4 or 5 wherein the form of hyaluronic acid is sodium hyaluronate in an amount of in excess of about 2200 mg and component (1) is diclofenac present in an amount of about 420 mg.

* * * * *